(12) United States Patent
Ronsen et al.

(10) Patent No.: US 6,660,298 B1
(45) Date of Patent: Dec. 9, 2003

(54) PAROXETINE TABLETS AND CAPSULES

(75) Inventors: Bruce Ronsen, River Forest, IL (US); Venkata R. Kota, Union, NJ (US); Yogesh Sadhale, Palatine, IL (US)

(73) Assignee: Pentech Pharmaceuticals, Inc., Wheeling, IL (US)

( * ) Notice: Subject to any disclaimer, the term of this patent is extended or adjusted under 35 U.S.C. 154(b) by 0 days.

(21) Appl. No.: 09/626,941

(22) Filed: Jul. 27, 2000

(51) Int. Cl.[7] .............. A61K 9/20; A61K 9/14; A61K 9/16
(52) U.S. Cl. .......... 424/465; 424/464; 424/489; 424/490; 424/493; 424/494
(58) Field of Search ............... 424/464, 489, 424/490, 465, 493, 494; 514/321

(56) References Cited

U.S. PATENT DOCUMENTS

| | | | | |
|---|---|---|---|---|
| 4,721,723 A | * | 1/1988 | Barnes et al. ........... | 514/321 |
| 5,227,379 A | * | 7/1993 | Jakobsen et al. ......... | 514/228.2 |
| 5,811,436 A | * | 9/1998 | Leonard et al. .......... | 514/321 |
| 5,955,475 A | * | 9/1999 | Krape et al. ............ | 514/321 |
| 6,168,805 B1 | * | 1/2001 | Hein, II et al. ......... | 424/465 |
| 6,214,386 B1 | * | 4/2001 | Santus et al. ........... | 424/489 |

FOREIGN PATENT DOCUMENTS

| | | |
|---|---|---|
| WO | WO 00/78288 A | 12/0000 |
| WO | WO 98/31365 A | 7/1998 |
| WO | WO 99/16440 A | 4/1999 |
| WO | WO 99/56751 A | 11/1999 |
| WO | WO 99/56751 | * 11/1999 |
| WO | WO 01/30349 A | 5/2001 |

OTHER PUBLICATIONS

Kristensen and Schaefer. (1987). *Drug Dev Ind Pharm* 13(4–5):.

Record. (1980). *Int J Pharm Prod Dev* 1:32–39.

* cited by examiner

*Primary Examiner*—Thurman K. Page
*Assistant Examiner*—S. Tran
(74) *Attorney, Agent, or Firm*—Morrison & Foerster LLP

(57) ABSTRACT

Method for preparing a wet granule formulation of paroxetine hydrochloride are disclosed. The formulations are suitable for tabletting and capsulation.

20 Claims, 13 Drawing Sheets

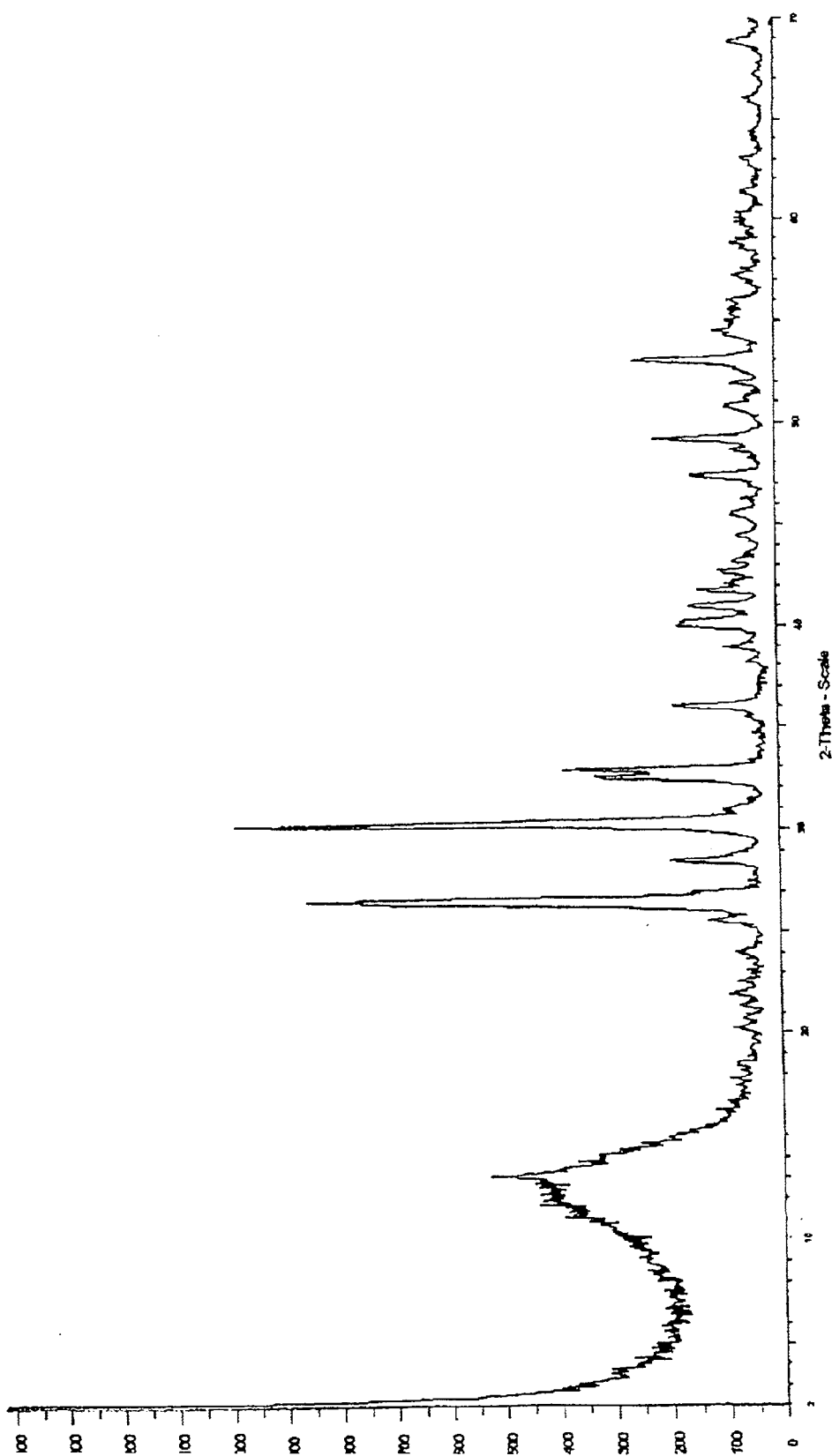
Figure 1: X-Ray Diffraction Pattern of paroxetine HCl granules made according to the process described in Example 2

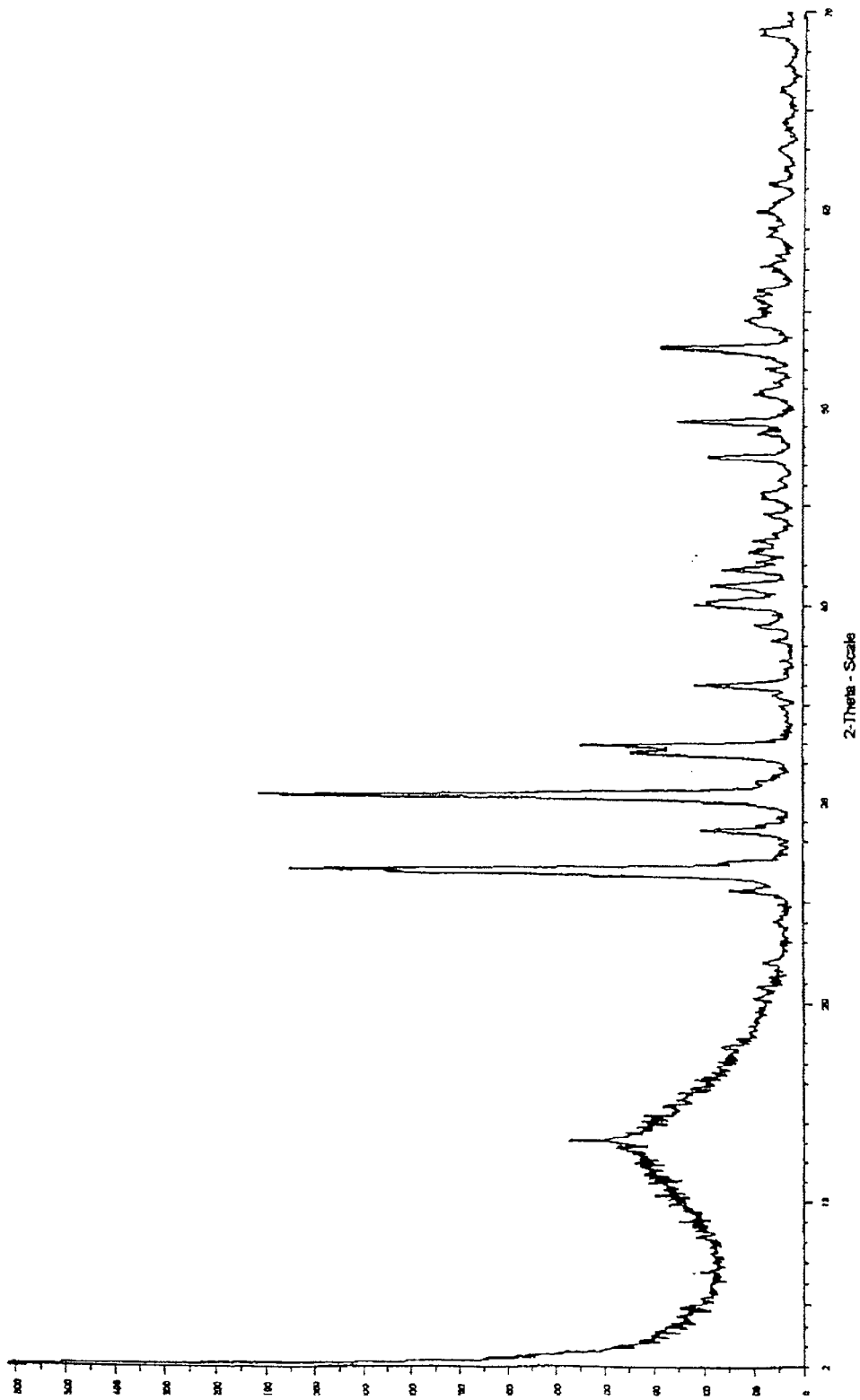
Figure 2: X-Ray Diffraction Pattern of placebo granules made according to the process described in Example 2

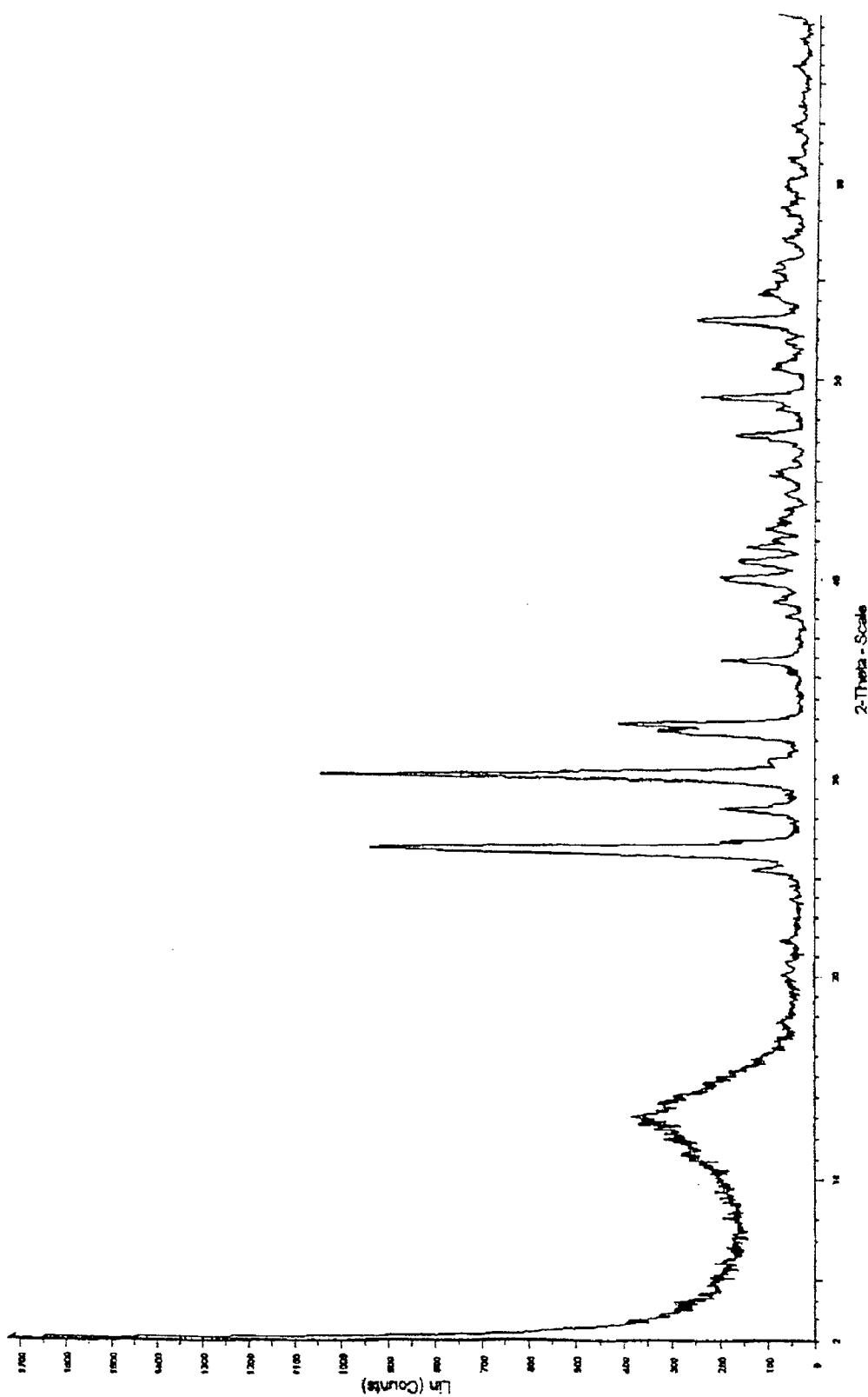
Figure 3: X-Ray Diffraction Pattern of a sample of dibasic calcium phosphate anhydrous used in Example 2

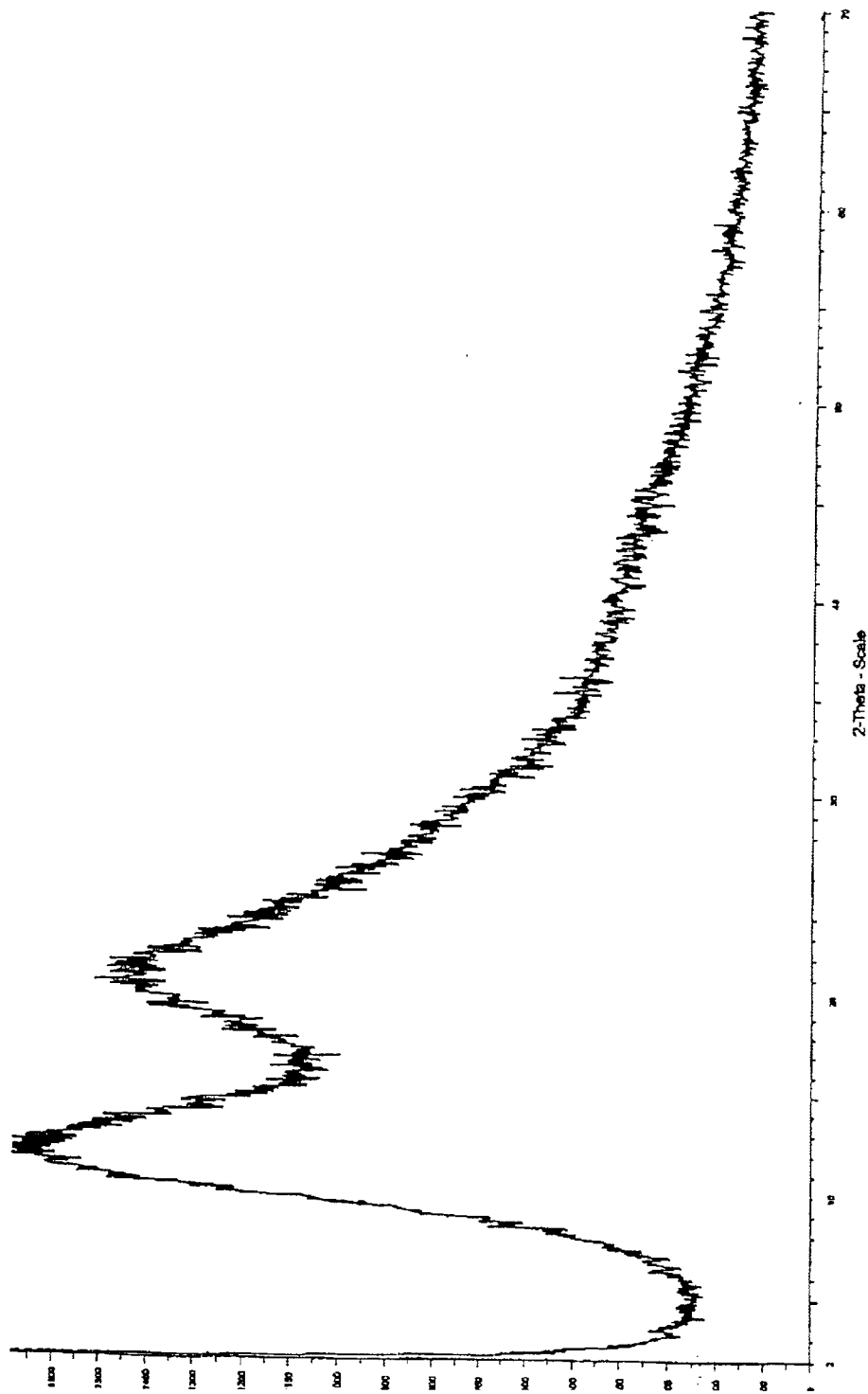
Figure 4: X-Ray Diffraction Pattern of a sample of PVP K-30 used in Example 2

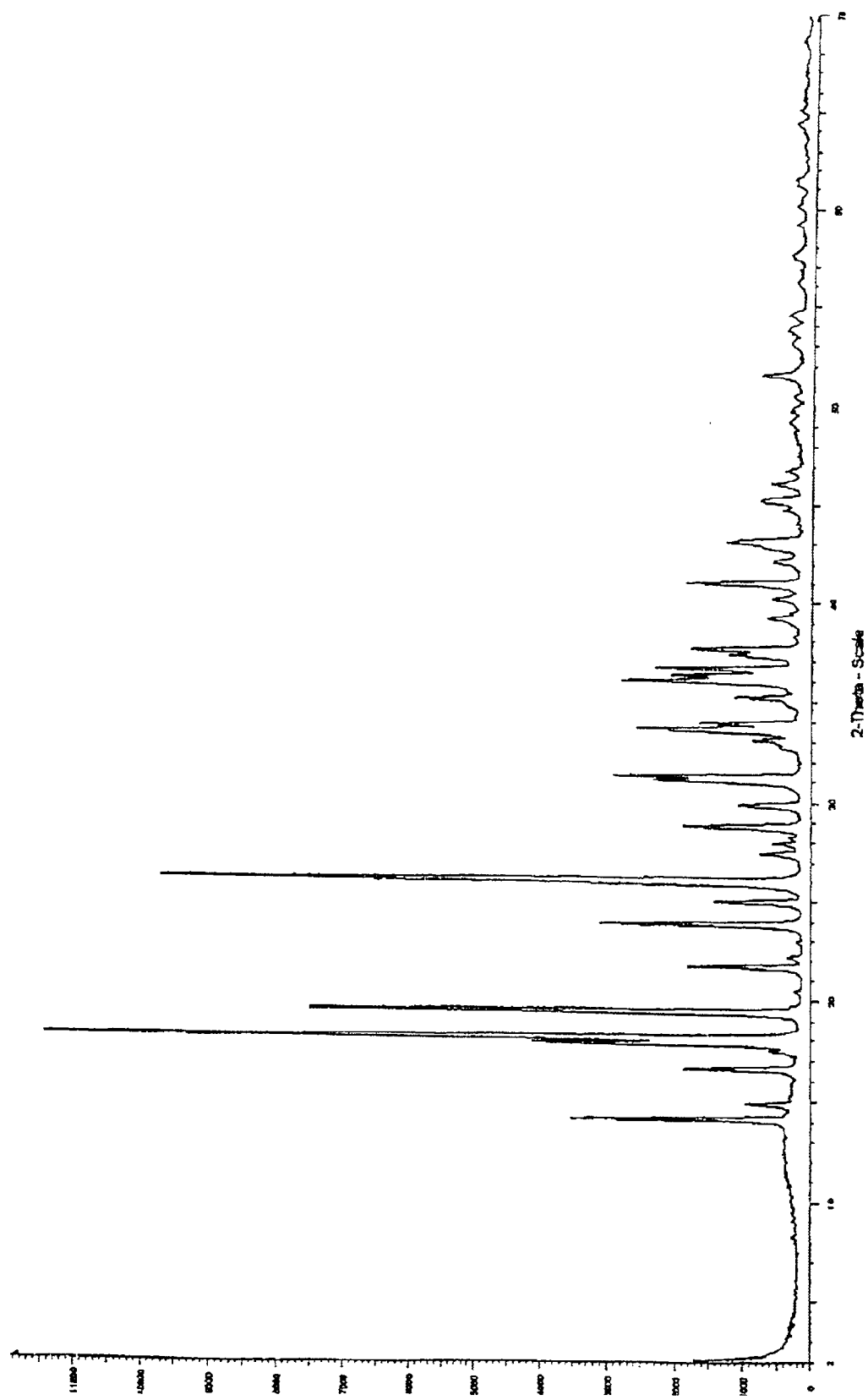
Figure 5: X-Ray Diffraction Pattern of a sample of citric acid anhydrous used in Example 2

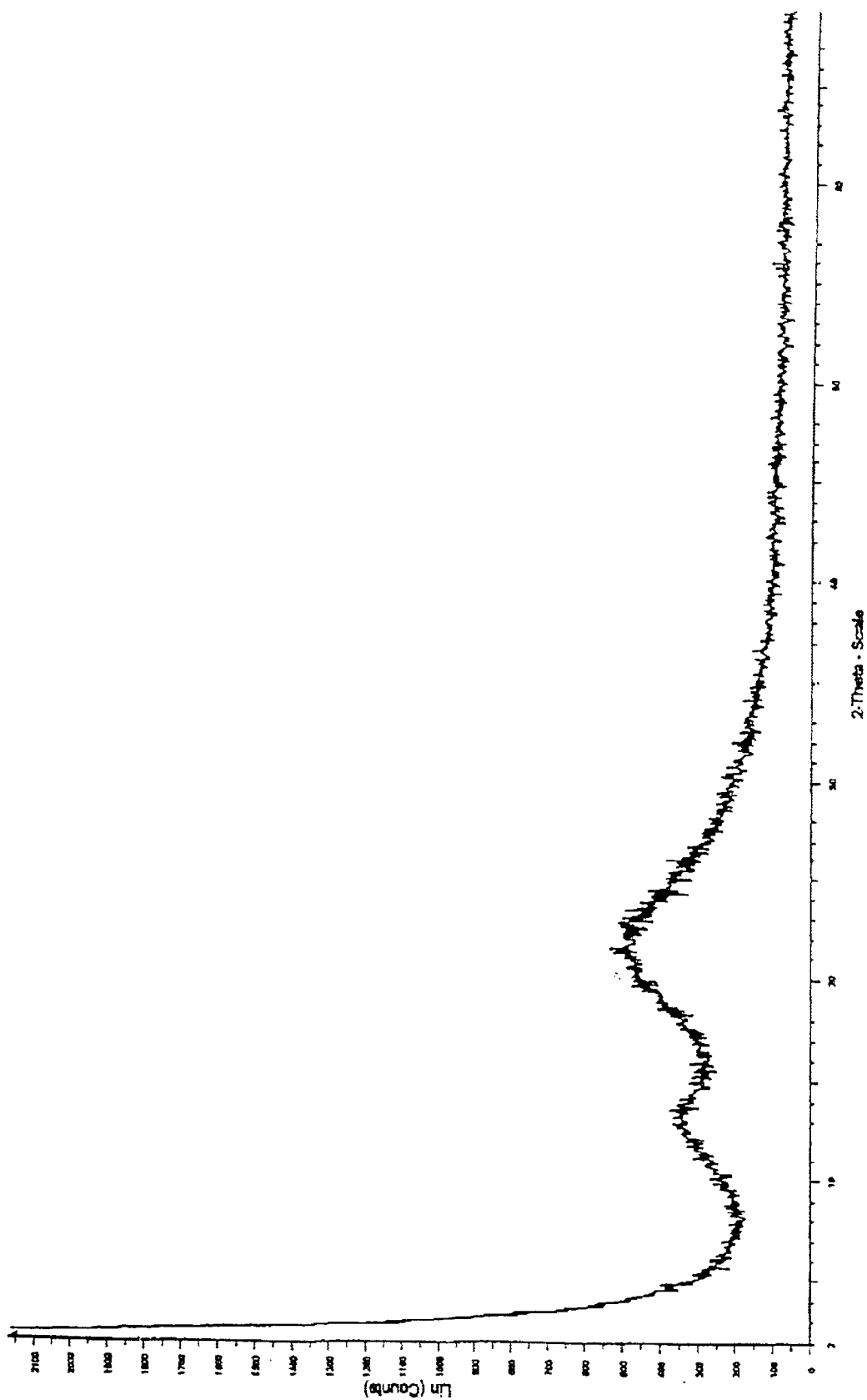
Figure 6: X-Ray Diffraction Pattern of a sample of colloidal silicon dioxide used in Example 2

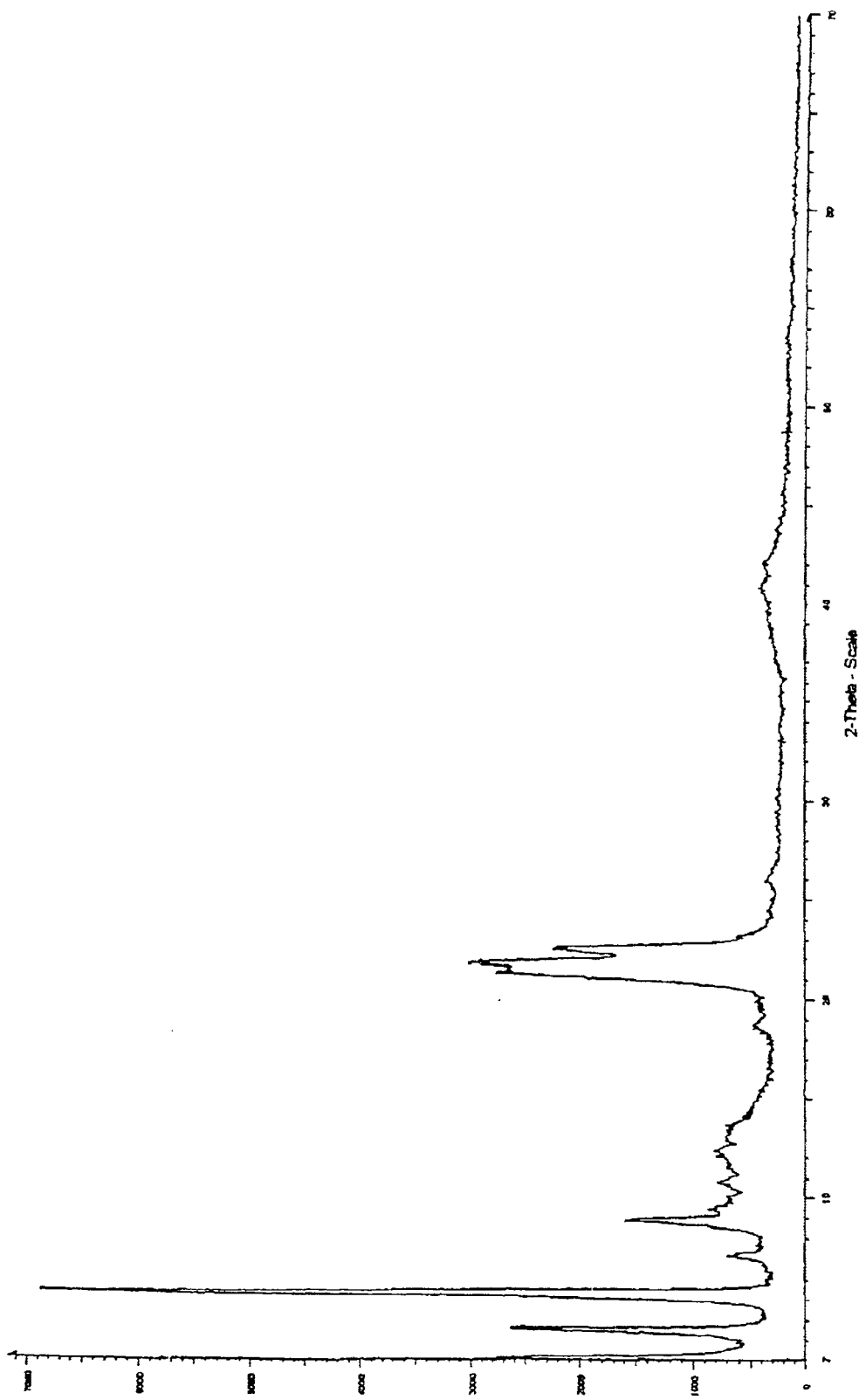
Figure 7: X-Ray Diffraction Pattern of a sample of magnesium stearate used in Example 2

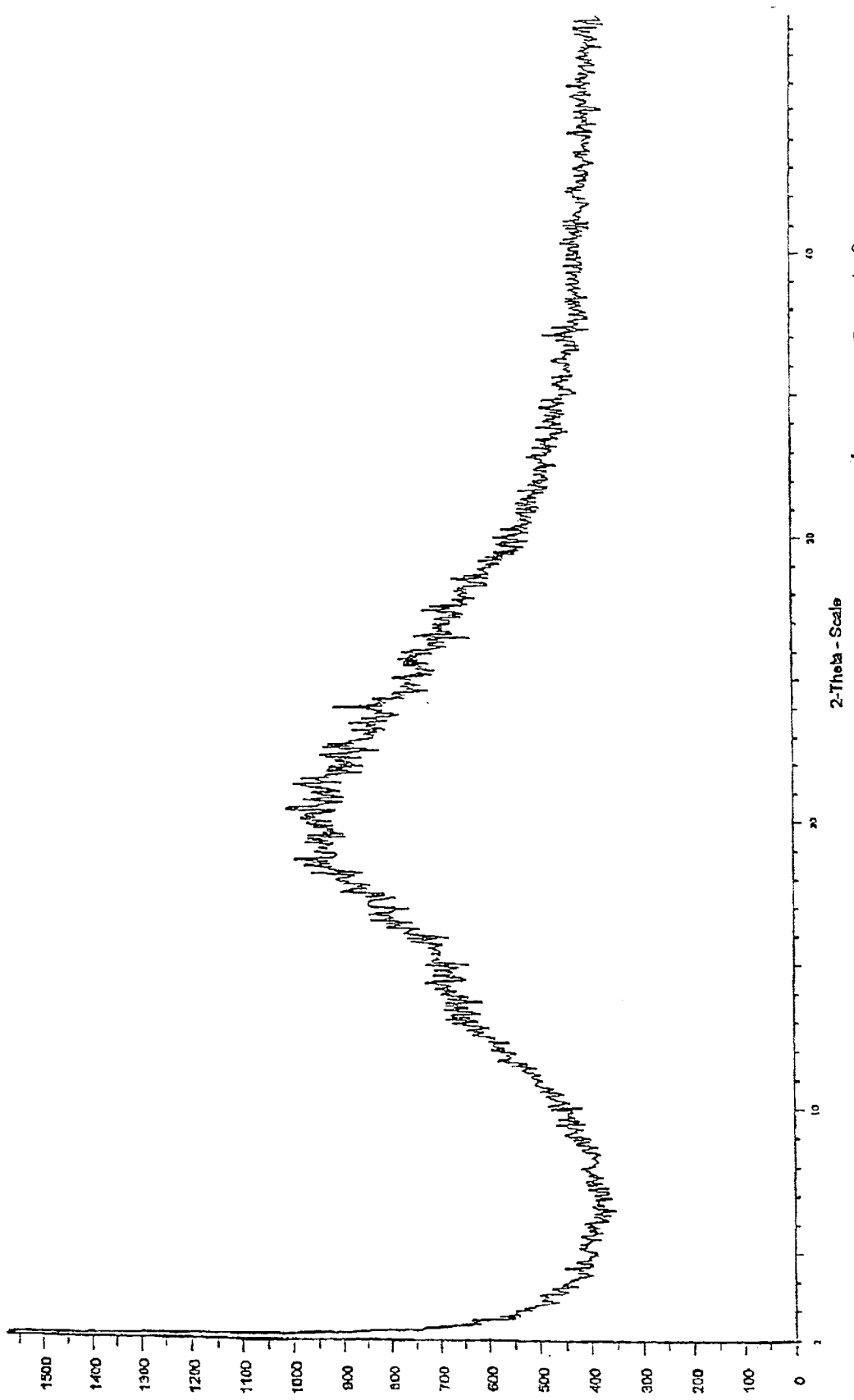
Figure 8: X-Ray Diffraction Pattern of a sample of amorphous paroxetine HCl used in Example 2.

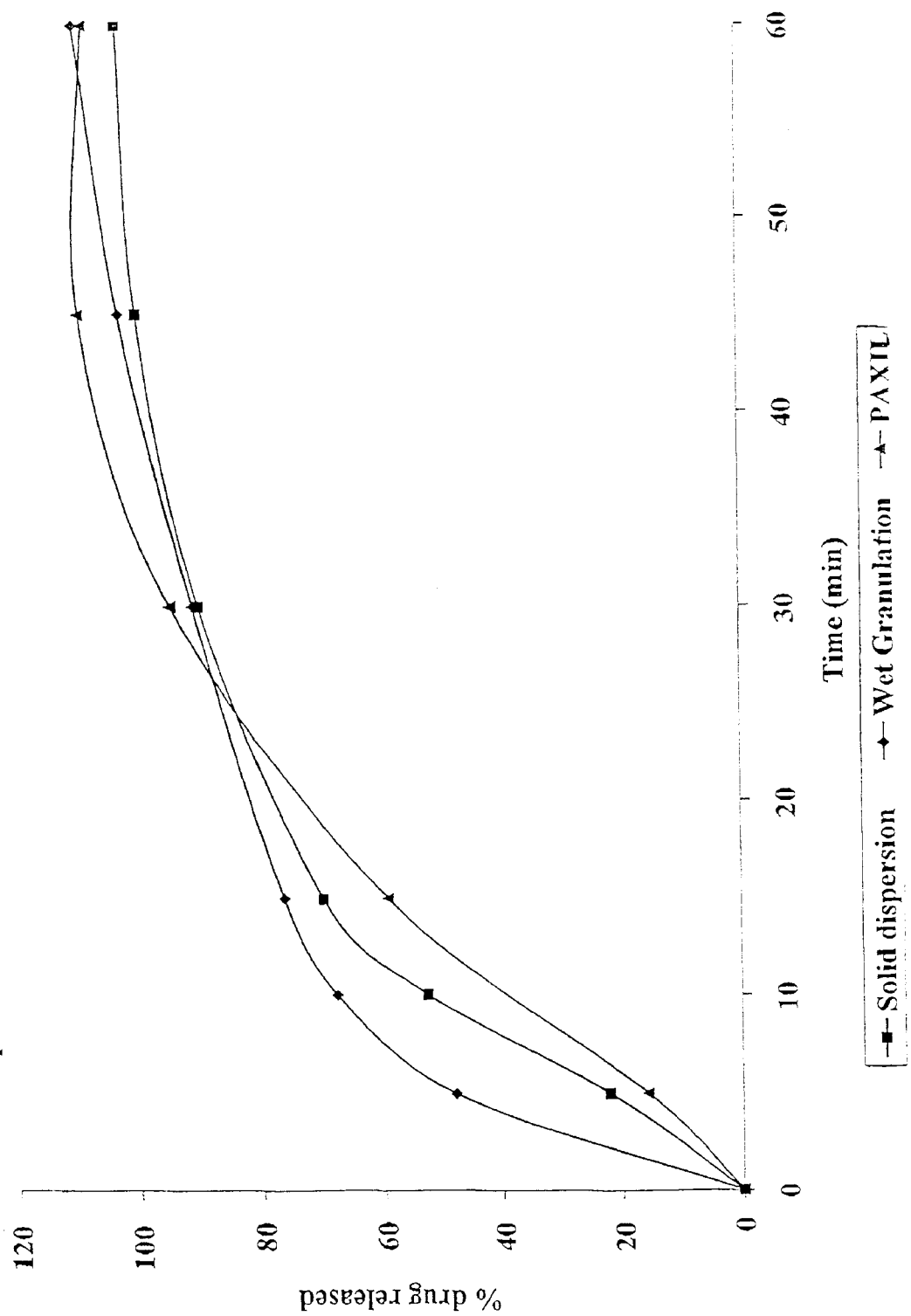
Figure 9: Comparative Dissolution Profiles of Paroxetine HCl 20 mg Capsules in Simulated Gastric Fluid (37°C, 60 rpm, n = 6)

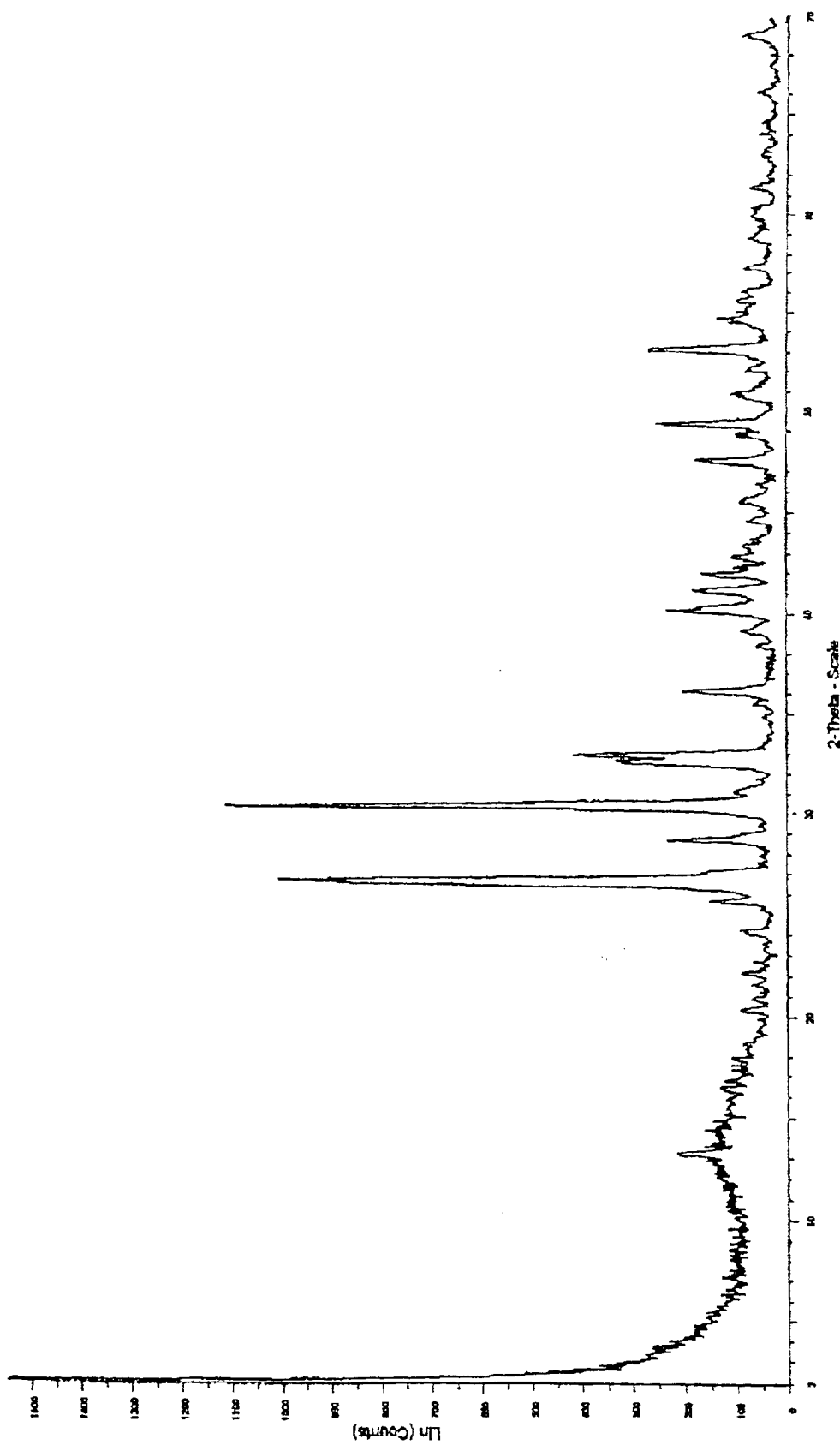
Figure 10: X-Ray Diffraction Pattern of paroxetine HCl granules made according to the process described in Example 3

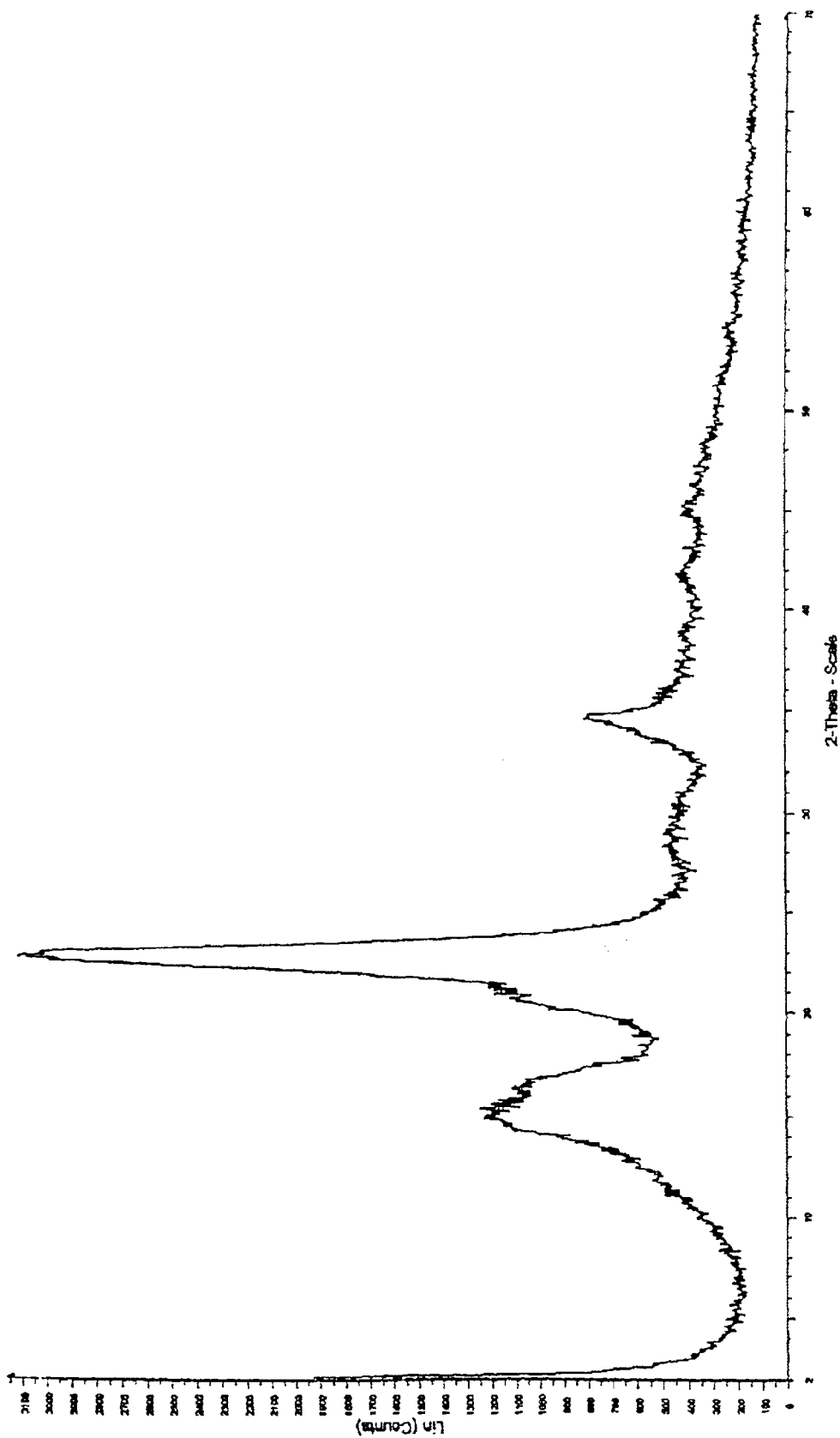
Figure 11: X-Ray Diffraction Pattern of paroxetine HCl granules made according to the process described in Example 4

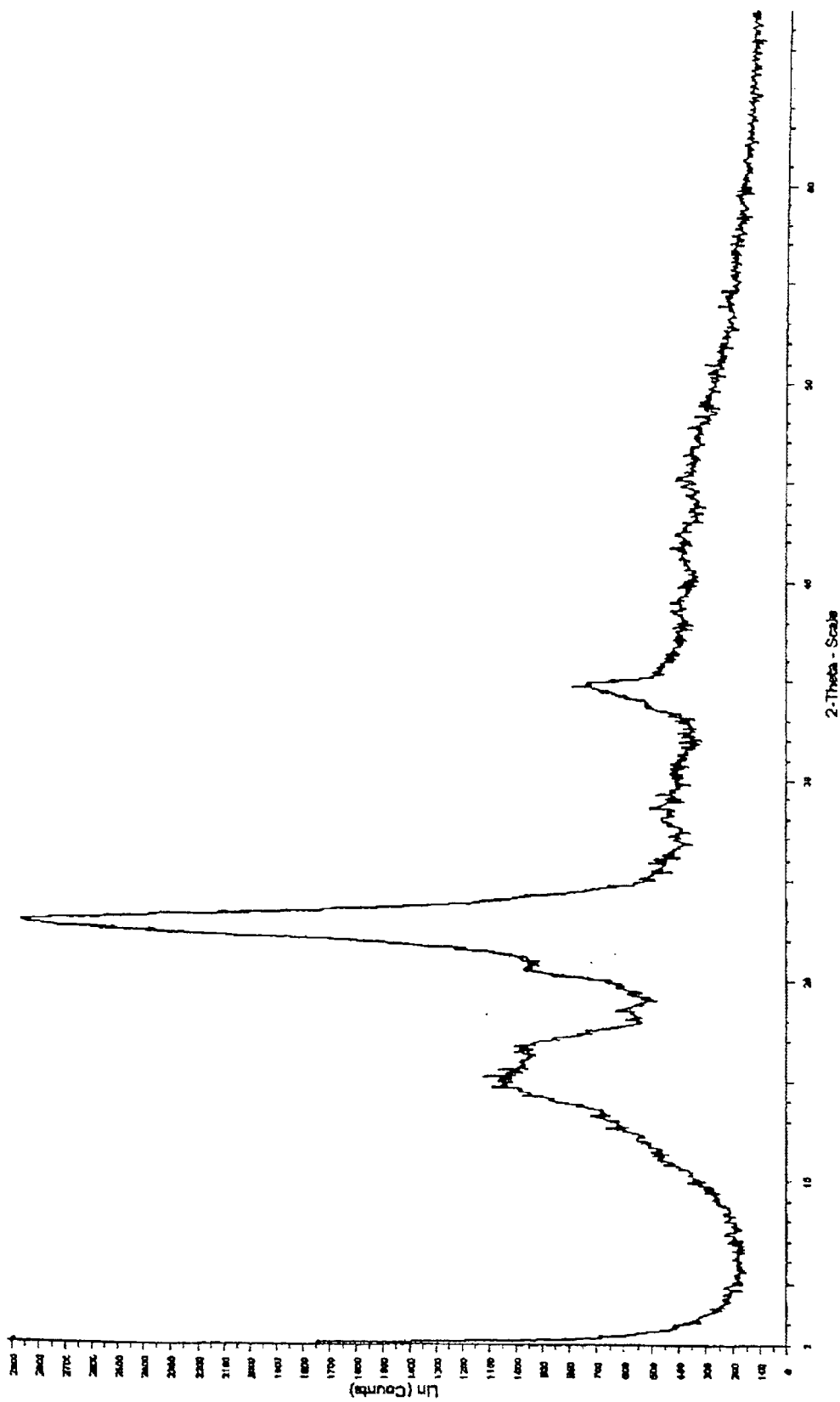
Figure 12: X-Ray Diffraction Pattern of placebo granules made according to the process described in Example 4

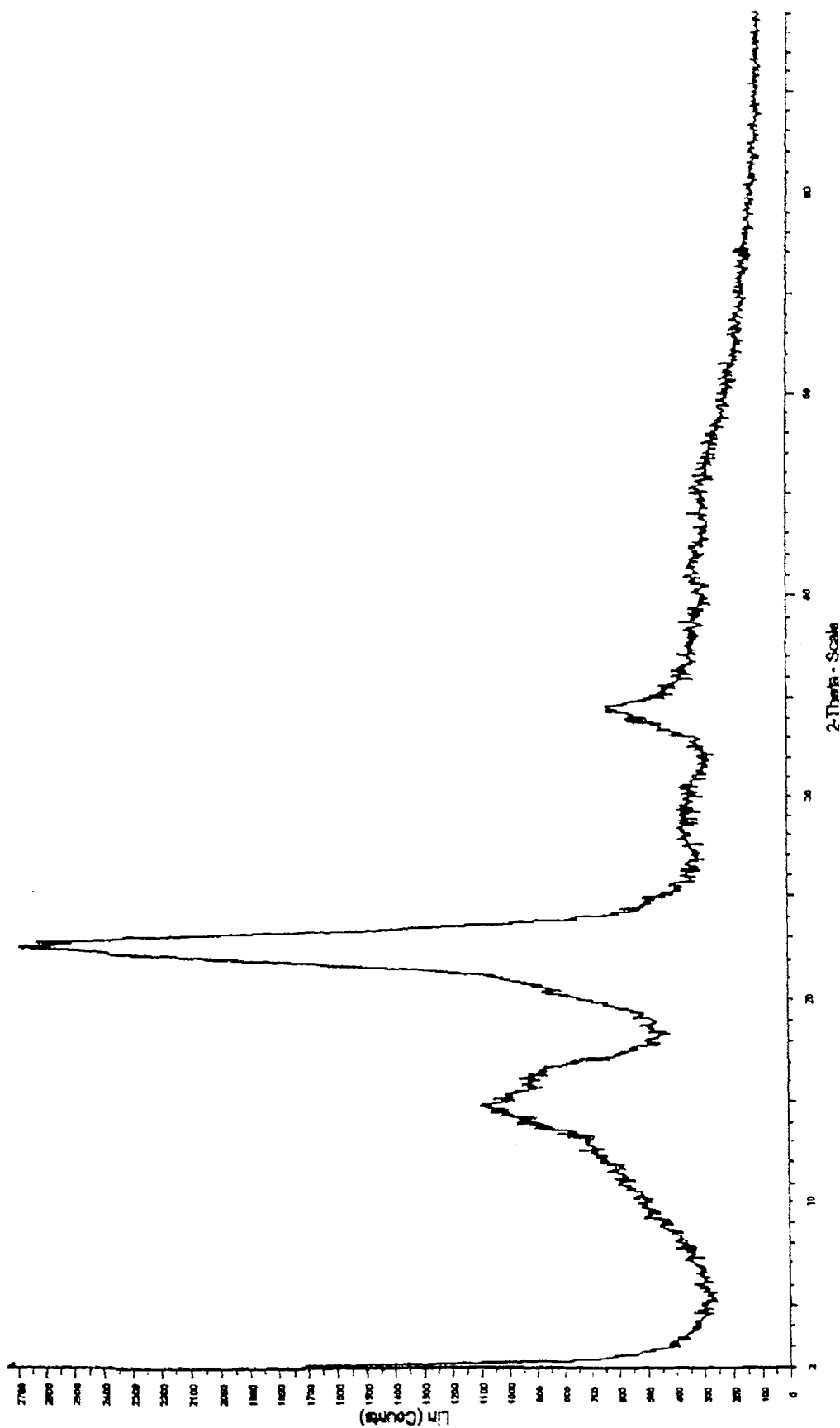
Figure 13: X-Ray Diffraction Pattern of a sample of Avicel Ph 113 used in Example 4

PAROXETINE TABLETS AND CAPSULES

TECHNICAL FIELD

By addition of an acidulent and a water dispersible polymer, a sufficient degree of solubility for paroxetine hydrochloride amorphous in aqueous solution can be achieved to permit a practical wet granulation method to be performed. These formulations are particularly useful for preparing capsules and tablets.

BACKGROUND ART

Wet granulation is the oldest and most conventional method of making tablets. This highly versatile process has been extensively reviewed by Record (*Int. J Pharm. Prod Dev.*, 1:32–39, 1980), Kristensen and Schaefer (*Drug Dev. Ind. Pharm.*, 13 (4 and 5):803–872, 1987) and Capes (*Handbook of powder Technology*, J. C. Williams and T. Allen, Eds., Elsevier, Amsterdam, 1980). *Pharmaceutical Dosage Forms: Tablets*, Volume 1, H. A. Lieberman, L. Lachman and J. B. Schwartz, Eds., 1989, lists some advantages of the wet granulation method. These are improvement in the cohesiveness and compressibility of powders, enhancement of the flow properties of the drug and/or excipients, improvement in the content uniformity of the blend, especially with low dose drugs, and improvement in the aesthetic elegance of the formulation by preventing problems such as non-uniform color distribution and/or color migration. Wet granulation has some disadvantages, such as the need for large number of processing steps which are time-consuming, the need for a number of pieces of expensive equipment, and slightly larger material losses. However, the superior quality of the final product and the versatility of the process normally outweighs these disadvantages.

One of the major parameters that needs to be controlled in wet granulation is the amount of granulating fluid used, so that the mass to be granulated and encapsulated or tabletted is merely moist and not wet or pasty. The amount of granulating fluid required to achieve this end depends on the total mass of filler, the amount of filler in the formulation and the solvent absorbing capacity of the filler. The active ingredient in the formulation must be sufficiently soluble in the granulating fluid to permit use of a quantity of fluid appropriate for the physical characteristics of the granulation formulation while supplying the requisite amount of drug.

Paroxetine HCl, the subject of the herein application, is used in the treatment of depression, pre-menstrual syndrome, social aversion disorder, premature ejaculation and other human and veterinarian conditions and diseases. Paroxetine HCl has been reported to be only slightly soluble in water (6 to 12 mg/ml). An amorphous form of paroxetine HCl has now been found to be soluble up to 75 mg/ml at room temperature. Even at this concentration, the wet formulation process would be less than conveniently feasible, as the quantity of solvent required to obtain a composition of desired strength would be too great to result in a tablet or capsule of reasonable size. This problem cannot be solved by granulating the paroxetine hydrochloride along with the filler (rather than dissolving it in the granulating fluid) because this would result in conversion of the amorphous form to the thermodynamically more stable crystalline form; a form with lower solubility that is less desirable.

It has now been found that the solubility of paroxetine hydrochloride can be increased sufficiently in a suitable granulation solvent to make the wet granulation process feasible.

DISCLOSURE OF THE INVENTION

The invention is directed to a method of formulating paroxetine hydrochloride using a wet granulation process and the resultant thereof, wherein the paroxetine hydrochloride retains its amorphous form and can readily be formulated into tablets and capsules. It has been found possible to solubilize amorphous paroxetine hydrochloride at a level of approximately 300 mg/ml which permits successful application of the wet granulation techniques.

Thus, in one aspect, the invention is directed to a method to prepare a formulation of paroxetine hydrochloride suitable for tabletting or encapsulation which method comprises sizing a dried mixture of at least one filler and an aqueous solution of paroxetine hydrochloride, which solution further comprises the combination of at least one water dispersible polymer and at least one acidulent, said combination present in sufficient concentration to solubilize the paroxetine hydrochloride to a level sufficient to provide a ratio of granulation solvent and filler that is satisfactory for tabletting and encapsulation. In another aspect, the invention is directed to wet granulation formulations prepared by the method of the invention and tablets and capsules prepared from them. The invention is also directed to methods to use the invention formulations.

In still another aspect, the invention is directed to a method to solubilize paroxetine HCl in aqueous solvents.

In still another aspect, the invention is directed to a method to formulate amorphous paroxetine hydrochloride into a wet granulated formulation wherein the process avoids any formation of crystalline forms, such as the hemihydrate.

BRIEF DESCRIPTION OF THE DRAWINGS

All of the drawings show X-ray diffraction patterns of final formulations, placebos, or components of the formulations. Exhibit A, which follows the figures in this submission, gives intensity values for these patterns.

FIG. 1 shows the X-ray diffraction pattern of paroxetine hydrochloride granules prepared by the method of the invention.

FIG. 2 is the X-ray diffraction pattern of placebo granules prepared by the invention method.

FIG. 3 is the X-ray diffraction pattern of dibasic calcium phosphate anhydrous used to prepare the formulations of FIGS. 1 and 2.

FIG. 4 is the X-ray diffraction pattern of PVP K-30 used to prepare the formulations of FIGS. 1 and 2.

FIG. 5 is the X-ray diffraction pattern of citric acid anhydrous used to prepare the formulations of FIGS. 1 and 2.

FIG. 6 is the X-ray diffraction pattern of colloidal silicon dioxide used to prepare the formulation of FIGS. 1 and 2.

FIG. 7 is the X-ray diffraction pattern of magnesium stearate used to prepare the formulations of FIGS. 1 and 2.

FIG. 8 is the X-ray diffraction pattern of amorphous paroxetine hydrochloride used to prepare the formulation of FIG. 1.

FIG. 9 shows the dissolution profile of the wet granulation formulation of the invention in comparison to that of a solid dispersion and in comparison to a commercial PAXIL tablet.

FIG. 10 is an X-ray diffraction pattern of paroxetine hydrochloride granules made according to an additional embodiment of the invention.

FIG. 11 is an X-ray diffraction pattern of paroxetine hydrochloride granules made according to still another embodiment of the invention.

FIG. 12 is the X-ray diffraction pattern of a placebo granule made according to the embodiment of FIG. 11.

FIG. 13 is the X-ray diffraction pattern of Avicel Ph 113 used in the embodiments of FIGS. 11 and 12.

MODES OF CARRYING OUT THE INVENTION

The invention provides superior formulations of paroxetine hydrochloride which can be obtained through a process of wet granulation. In the wet granulation process, a solution containing the active ingredient, in this case, paroxetine hydrochloride, along with solubilizing ingredients therefor is admixed with a solid filler which may comprise one or more components, and articulated so as to obtain a uniform mixture which is moist, but not wet or pasty. Thus, the mixture is not a slurry, but rather a moist articulated solid. The filler solid is mixed uniformly with the solution of the drug using, for example a planetary mixer, ribbon blender, twin-shell V-blender with an intensifier bar, standard kitchen mixer, a stirring bar, kneading, for example, with a mortar and pestle, or any other standard method of achieving a uniform composition. The uniform mixture is then dried; the drying can be accomplished using elevated temperatures and ambient pressure, such as in a convection oven or a fluid bed dryer. Typical drying temperatures for the methods of the present invention are in the range of 40–80° C., typically 50–70° C. or most preferably at about 60° C. The time for the drying step is determined by the quantity of material and the physical configuration—for example, thin films dry more readily than thicker composites. Thin films are preferred. The drying process typically takes several hours. The dried composition is then granulated or sized by any conventional means, such as forcing the dried composition through a sieve or other milling procedure. The resulting composition is a free-flowing powder. It can be supplemented with additional solids which are processing aids such as colloidal silica, magnesium stearate, and the like, as well as talc, stearic acid, zinc stearate, calcium stearate, fumaric acid, sodium fumarate, polyethylene glycols, hydrogenated castor oil, Tweens, Spans, and sodium lauryl sulfate. The granules can then be used directly to fill gelatin capsules or can be compressed into tablets, or otherwise manipulated to obtain desired dosage forms.

The present invention is made possible by the ability to dissolve paroxetine hydrochloride to a suitable level in a fluid which is appropriate for the wet granulation method. The active ingredient must be made sufficiently soluble that a volume of fluid which contains an adequate dose will not require an undue amount of filler in order to achieve the correct level of moisture, resulting in a tablet or capsule that is too voluminous to be practical. Thus, the importance of achieving adequate solubility of the drug is clear. It has now been found that paroxetine hydrochloride, regardless of its initial form, can be solubilized in aqueous solutions by supplementing the aqueous solution with a combination of at least one water dispersible polymer and at least one acidulent. Aqueous alcoholic solutions may also be used. Using this combination, and, optionally, elevated temperatures, sufficient solubility can be obtained. For paroxetine hydrochloride, solubility levels of at least 200 mg/ml, preferably at least 250 mg/ml, and more preferably at least 300 mg/ml are achievable by this method.

The paroxetine hydrochloride used in the invention method is preferably the amorphous form; however, crystalline anhydrate, crystalline hydrates, and any other initial form may be used in the method of the invention if the required solubility can be achieved.

The solvent is an aqueous solvent or an alcohol/aqueous solvent. The aqueous solvent may contain a C1–C5 alcohol to the extent of mutual solubility, taking account of potential toxicity of residuals after drying and the boiling point of the alcohol. Ethanol is preferred since it is miscible with water and is not particularly toxic and can be included at concentrations up to 25%. In addition to ethanol, other alcohols, such as isopropanol and n-propanol, mixtures of alcohols including polyols, can be included. The aqueous or alcohol/aqueous solvent may also include inorganic salts and/or sugars.

The granulation fluid contains at least one water dispersible polymer and at least one acidulent. The water dispersible polymer may comprise, for example, polyethylene glycol, various forms of starch or cellulose, such as Methocel or Ethocel, and/or other polymers such as esters of polyvinyl alcohol; or a commercial carbomer, such as carbopol 974P, as well as natural gums such as acacia, tragacanth, guar gum, agar-agar, etc., gelatin, sodium alginate, chitosan, water-soluble cyclodextrins such as hydroxypropyl β-cyclodextrin, methacrylic acid derivatives, phthalates, and the like. A preferred polymer is polyvinyl pyrrolidone.

The fluid will also contain at least one acidulent, such as citric acid, tartaric acid, glutamic acid and the like. Additional embodiments include fumaric acid, malic acid, ascorbic acid, succinic acid, hydrochloric acid and salts thereof to the extent acidity remains as a property. Particularly preferred as an acidulent is citric acid either alone or in combination with another one or more acids.

Preferred concentrations of the water soluble polymer are in the range of about 50–500 mg/ml, preferably in the range of 100–400 mg/ml. The precise concentration will depend on the nature of the water dispersible polymer. The concentration of the acidulent will depend on the nature of the compound, but can be as low as, for example, 5 mg/ml citric acid or less. A wide range of concentrations of the acidulent is possible as indicated in the examples below.

It may be desirable to heat the solution in order to effect greater solubility of the paroxetine hydrochloride. The solution may safely be heated to 50–70° C., preferably around 60° C. Heating the solution also is helpful in the drying process.

In the method described above, aqueous solutions of paroxetine at concentrations of at least 75 mg/ml, preferably 150 mg/ml, more preferably 200 mg/ml, and still more preferably 250 mg/ml or 300 mg/ml based on the weight of paroxetine hydrochloride amorphous can be achieved. While typically the hydrochloride is employed, other salts of paroxetine which have comparable inherent solubility can be used.

Suitable fillers with which the dissolved paroxetine hydrochloride may be mixed include inorganic salts, such as dibasic calcium phosphate anhydrous (DPCA), microcrystalline cellulose, starch, celite, silica, gelatin, albumin, talc, mannitol and other sugars, corn starch and corn cob (pulverized). A suitable list might include sugars such as sucrose, lactose, maltose, dextrose, mannitol, xylitol, starches, celluloses such as microcrystalline cellulose, silicified microcrystalline cellulose, hydroxypropyl methylcellulose, hydroxypropyl cellulose, methyl cellulose, ethyl cellulose, carboxymethyl cellulose sodium, inorganic salts such as dibasic calcium phosphate, calcium phosphate, calcium sulfate, sodium phosphate, calcium carbonate, magnesium carbonate, maltodextrins, lactates, etc.

As shown in the examples below, addition of polyvinyl pyrrolidone and citric acid in an aqueous-alcoholic or simple aqueous mixture containing up to 25% ethanol results in solubility of paroxetine HCl of above 300 mg/ml. At these higher levels of paroxetine HCl, solubility the amount of granulating solvent required can be reduced, and crystallization of the drug is eliminated. The increased solubility and stability of the drug solution makes possible formulation of the drug by a heretofore unfeasible method.

In addition, as demonstrated below, the process of the invention is such that crystalline paroxetine hydrochloride such as the hemihydrate or an alternative crystalline form is not formed during the process nor is it present in the final formulation. This is particularly advantageous as the formulated amorphous paroxetine hydrochloride itself has enhanced solubility in comparison with the hemihydrate.

Briefly, and in summary, present invention provides an economical and environmentally compatible manufacturing process for the preparation of a paroxetine HCl granulation suitable for producing stable tablets and/or capsules of this therapeutic agent for the treatment of depression and/or premature ejaculation or other indications for which paroxetine is useful. In the method, an aqueous solution of the paroxetine HCl, preferably heated which contains at least one water dispersible polymer and at least one acidulent is admixed with filler, such as dicalcium phosphate, anhydrous and dried and sized. The aqueous solution will contain up to and including 40% w/v paroxetine HCl, with complete solubility at up to 25% ethanol and at 50° C. The solution is sorbed onto the filler, and is dried at temperatures of about 50° C. or higher. The dry mass is sized typically by passing it either through a milling device or directly passing the mass through a wire screen of a known mesh. The final granules are blended with any desired additional processing aids, such as colloidal silica, magnesium stearate, etc., or additional filler to adjust the strength of the granulation. The granulation can be used directly to either fill gelatin capsules or to produce tablets by compressing the granulation.

The following examples are intended to illustrate but not to limit the invention.

Preparation A

Determination of Solubility

Approximately 45, 100, 200, 300, 400, 500, 510, 750 and 1000 mg of amorphous paroxetine HCl were weighed into nine 25-ml volumetric flasks labeled 1 through 9 respectively. Ten milliliters of deionized water were pipetted into each of the flasks and the flasks were stoppered. The flasks were then placed in a sonicator (Branson 1210, Danbury, Conn.) and sonicated for ten minutes taking care to see that there was no heating. After ten minutes, clear solutions were obtained in flasks 1 through 8 while flask 9 showed a clear solution with a slight precipitate at the bottom. Even after standing for 24 hours, the solutions in flasks 1 through 8 were clear while that in flask 9 still showed a clear solution with some precipitate. Thus, solutions of amorphous paroxetine HCl with a maximum solubility of about 75 mg/ml at room temperature were prepared.

Preparation B

Solubility in Aqueous Alcohol

A. Exactly two milliliters of ethanol were added to each of the nine flasks from Preparation A and the flasks shaken gently by hand. The solutions in flasks 1 through 8 stayed clear while that in flask 9 became clear indicating that at least 1 gram of amorphous paroxetine HCl could be dissolved in a hydroalcoholic solvent mixture containing about 15% ethanol.

B. Approximately 250, 320, 400, 570 and 1120 mg of amorphous paroxetine HCl were weighed into five 25-ml volumetric flasks labeled 1 through 5 respectively. Ten milliliters of ethanol-water mixture containing 20% v/v ethanol were pipetted into each of the flasks and the flasks were stoppered. The flasks were then placed in a sonicator (Branson 1210, Danbury, Conn.) and sonicated for ten minutes taking care to see that there was no heating. After ten minutes, clear solutions were obtained in flasks 1 through 4 while flask 5 showed a clear solution with a slight precipitate at the bottom.

Preparation C

Solubilization Enhancement

Approximately 1.0, 1.5, 1.6, 2.5 and 3.0 grams of amorphous paroxetine HCl were weighed into five 25-ml volumetric flasks. Ten milliliters of an ethanol-water (20% v/v ethanol) mixture containing 0.25 grams of polyvinyl pyrrolidone (PVP) K-30 and 0.02 grams of citric acid anhydrous were added into each of the five flasks and the flasks were sonicated for 30 minutes. Only the solution in flask 1 became clear while only part of the paroxetine HCl in flasks 2 through 5 dissolved. However, upon heating the flasks to about 60° C., all the solutions became clear.

EXAMPLE 1

Granulation Formulation 1

Approximately 1.6 grams of amorphous paroxetine HCl was weighed into a flask. To the flask was added 5 ml of 20% v/v ethanol in water containing 0.25 grams of PVP K-30 and 0.02 grams of citric acid anhydrous. The contents were heated to 60° C. in a water-bath till the paroxetine HCl dissolved completely. This solution was then added to 17.0 grams of dibasic calcium phosphate anhydrous (DCPA) in a mortar and mixed with a pestle. After the DCPA was uniformly mixed, the wet mass was transferred to a glass tray and dried in a convection oven at 50° C. for 1.5 hours. The dry mass was sized through a #50 mesh screen and the granules so obtained were lubricated with 0.06 grams of colloidal silicon dioxide and 0.04 grams of magnesium stearate. These granules can either be filled in capsules or compressed into tablets of desired weight.

EXAMPLE 2

Granulation Formulation 2

A. Preparation

Approximately 28.00 grams of amorphous paroxetine HCl was weighed into an Erlenmeyer flask. To the flask was added 95 ml of 20% v/v ethanol in water containing 29.79 grams of PVP K-30 and 1.79 grams of citric acid anhydrous. The contents were heated to 60° C. in a water-bath till the paroxetine HCl dissolved completely. This solution was then slowly added to 316.63 grams of dibasic calcium phosphate anhydrous (DCPA) in a mixer set at a speed setting of 125 rpm. After the solution was completely added, the mass was mixed for 15 minutes. After the DCPA was uniformly mixed, the wet mass was spread evenly in a thin bed onto two glass trays and dried in a convection oven at 50° C. for 6 hours. The dry mass was sized through a #50 mesh screen and the granules so obtained were lubricated with 1.25 grams of colloidal silicon dioxide and 0.83 grams of magnesium stearate to obtain granules.

B. Tabletting and Encapsulation

The granules made according to paragraph A were filled into empty size 2 capsules on a Feton (Brussels, Belgium)

manual encapsulating machine at an average fill weight of about 300 milligrams. Alternatively the granules were compressed with appropriate tooling on a Stokes Model F single punch tablet press into tablets, each with an average weight of about 300 mg and 20 mg strength.

C. Analysis by X-ray Diffraction

The granules made according to paragraph A were examined under the polarized light of an optical microscope (Leica DMLB, Germany). No birefringence was observed indicating that the amorphous paroxetine HCl had not crystallized out during the granulation process. The granules were also analyzed by X-Ray Powder Diffraction (XRPD) and the diffractogram compared with that of placebo granules made without paroxetine HCl using the same process. The patterns were obtained n a Siemens D5000 diffractometer using Cu Kα radiation, operated at 40 kV/30 mA by scanning from 2 to 70° C. 2θ, with a step size of 0.05° and an acquisition time of 2 seconds per step, with the sample spinning. The patterns, shown in FIGS. 1 and 2 respectively, were almost overlapping indicating that there was no process-induced change in the physical form of the drug. It will be evident that the paroxetine hydrochloride is maintained in amorphous form and does not form any hemihydrate. FIGS. 3 through 8 show the diffraction patterns of DCPA, PVP K-30, citric acid anhydrous, colloidal silicon dioxide, magnesium stearate and paroxetine HCl amorphous used in the above process.

D. Dissolution Studies

1) Three samples, the wet granulation capsule product of paragraph B, 2) a product prepared as a solid dispersion of paroxetine HCl, amorphous with polyvinyl pyrrolidone and citric acid blended with DCPA, colloidal silicon dioxide and magnesium stearate, and 3) a reference tablet marketed by SmithKline Beecham (PAXIL) were analyzed for dissolution rate. USP type 1 apparatus was used for the capsule product and for the solid dispersion and USP type 2 for the reference tablet. The media in each case were 900 ml of simulated gastric fluid without pepsin. The rotational speed of the apparatus is 60 rpm. The bath temperature is set at 37° C. The kettles (6) were sampled at predetermined time intervals and the drug released was measured against a reference lot. The results are shown in FIG. 9. As seen, the granulated product has a higher initial dissolution rate than the other two forms.

EXAMPLE 3

Granulation Formulation 3

Approximately 2.38 grams of PVP K-30 and 0.15 grams of citric acid anhydrous were weighed into a 25-ml Erlenmeyer flask and dissolved in 7.5 ml of deionized water by heating to 60° C. Approximately 2.23 grams of paroxetine HCl was weighed and added to the hot solution of PVP and citric acid and dissolved completely. This solution was then slowly added to 25.32 grams of dibasic calcium phosphate anhydrous (DCPA), prescreened through a #50 mesh screen, in a porcelain mortar. After the solution was completely added, the mass was manually kneaded with the help of a pestle. The wet mass was spread evenly in a thin bed onto a glass tray and dried in a convection oven at 60° C. for 2 hours. The dry mass was sized through a #50 mesh screen and the granules so obtained were examined under the polarized light of an optical microscope (Leica DMLB, Germany). No birefringence was observed indicating that the amorphous paroxetine HCl had not crystallized out during the granulation process. A small sample was analyzed by XRPD and the diffraction pattern is shown in FIG. 10. It was again confirmed that no hemihydrate formed in the process.

EXAMPLE 4

Granulation Formulation 4

Approximately 23.7 grams of PVP K-30 and 1.39 grams of citric acid anhydrous were weighed into a 500-ml beaker and dissolved in 250 ml of deionized water by heating to 65° C. Approximately 22.3 grams of paroxetine HCl was weighed and added to the hot solution of PVP and citric acid and dissolved completely. Approximately 251.17 grams of microcrystalline cellulose (Avicel PH 113) preheated to 70° C. for 2 hours was weighed out and warmed in an oven at 70° C. for 10 minutes. The preheated Avicel was granulated with the hot solution of drug, PVP and citric acid in a mixer at 125 rpm kneading for 10 minutes. The beaker was rinsed with 50 ml of warm water and the rinsing was added to the kneaded mass. The wet mass was spread evenly in a thin bed onto two glass trays and dried in a convection oven at 70° C. for 6 hours. The dry mass was sized through a #35 mesh screen. Placebo granules were made without paroxetine HCl using the same procedure. Samples of both the active and placebo granules were analyzed by XRPD and the diffraction patterns are shown in FIGS. 11 and 12 respectively. FIG. 13 shows the diffraction pattern of a sample of Avicel PH 113 used for making the granules. It was again confirmed that no hemihydrate formed in the process.

What is claimed is:

1. A method to prepare a formulation of paroxetine hydrochloride suitable for tabletting and encapsulation which method comprises sizing a dried mixture of (a) at least one filler and (b) an aqueous solution comprising paroxetine hydrochloride at a concentration of at least 150 mg/ml and a combination of an acidulant and a water dispersible polymer, said combination present in an amount effective to solubilize sufficient paroxetine hydrochloride to include an adequate dose of paroxetine hydrochloride with an amount of filler suitable for encapsulation or tabletting.

2. The method of claim 1 wherein said formulation is free of paroxetine hydrochloride in crystalline form.

3. The method of claim 1 which further includes mixing the dried and sized formulation with at least one further processing aid to obtain a further processed formulation.

4. The method of claim 3 wherein said further processed formulation, does not contain paroxetine hydrochloride in crystalline form.

5. The method of claim 1 which further includes tabletting or encapsulating the dried and sized formulation to obtain tablets or capsules.

6. The tablets or capsules of claim 5 wherein said paroxetine hydrochloride is free of the crystalline form.

7. The method of claim 1 wherein the acidulant is citric acid.

8. The method of claim 1 wherein the water dispersible polymer is polyvinyl pyrrolidone (PVP).

9. A granulated formulation of paroxetine hydrochloride prepared by the method of claim 1.

10. The formulation of claim 9 wherein said paroxetine hydrochloride is free of the crystalline form.

11. Tablets or capsules prepared by the method of claim 3.

12. Tablets or capsules of claim 11 wherein the paroxetine hydrochloride is free of the crystalline form.

13. A method to treat a condition benefited by paroxetine hydrochloride which method comprises administering to a subject in need of such treatment an effective amount of the formulation of claim 9.

14. A method to treat a condition benefited by paroxetine hydrochloride which method comprises administering to a subject in need of such treatment an effective amount of the tablets or capsules of claim 11.

15. The method of claim 1, wherein the acidulant is selected from the group consisting of citric acid, tartaric acid, glutamic acid, fumaric acid, malic acid, ascorbic acid, succinic acid, hydrochloric acid, and a combination thereof.

16. The method of claim 1, wherein the filler is dibasic calcium phosphate anhydrous.

17. The method of claim 1, wherein the filler is microcrystalline cellulose.

18. The method of claim 1, wherein the aqueous solution comprises paroxetine hydrochloride at a concentration of at least 200 mg/ml.

19. The method of claim 1, wherein the aqueous solution comprises paroxetine hydrochloride at a concentration of at least 250 mg/ml.

20. The method of claim 1, wherein the aqueous solution comprises paroxetine hydrochloride at a concentration of at least 300 mg/ml.

* * * * *